(12) United States Patent
Moir et al.

(10) Patent No.: US 6,995,837 B1
(45) Date of Patent: Feb. 7, 2006

(54) OPTICAL INSPECTION SYSTEM AND METHOD OF USE

(75) Inventors: Floyd W. Moir, Seymour, CT (US); Karl Cressotti, Cheshire, CT (US)

(73) Assignee: Retina Systems Inc., CT (US)

( * ) Notice: Subject to any disclaimer, the term of this patent is extended or adjusted under 35 U.S.C. 154(b) by 81 days.

(21) Appl. No.: 10/775,786

(22) Filed: Feb. 10, 2004

(51) Int. Cl.
*G01N 21/00* (2006.01)

(52) U.S. Cl. .................................... 356/237.1
(58) Field of Classification Search ............. 356/237.1, 356/237.2, 237.4, 237.5; 209/586, 929, 904, 209/907, 922, 923, 652, 228, 576
See application file for complete search history.

(56) References Cited

U.S. PATENT DOCUMENTS

| | | | | |
|---|---|---|---|---|
| 3,709,328 A | * | 1/1973 | Mohr et al. .................. 209/586 |
| 5,777,246 A | * | 7/1998 | Woods et al. ............... 73/865.8 |
| 5,823,356 A | * | 10/1998 | Goodrich et al. ........... 209/601 |
| 5,918,727 A | * | 7/1999 | Wallace et al. .......... 198/690.1 |
| 6,055,329 A | * | 4/2000 | Mufti ......................... 382/152 |
| 6,072,583 A | * | 6/2000 | Kellner ....................... 356/614 |
| 6,285,034 B1 | * | 9/2001 | Hanna et al. ............. 250/559.2 |
| 6,762,426 B1 | * | 7/2004 | Gilliam .................. 250/559.12 |
| 6,787,724 B2 | * | 9/2004 | Bennett et al. ............. 209/586 |
| 2004/0114113 A1 | * | 6/2004 | Yamada et al. ............... 353/61 |
| 2005/0094861 A1 | * | 5/2005 | Prakash et al. ............. 382/137 |

* cited by examiner

*Primary Examiner*—Gregory J. Toatley, Jr.
*Assistant Examiner*—Ali Allawi
(74) *Attorney, Agent, or Firm*—John H. Crozier

(57) ABSTRACT

In a preferred embodiment, an optical inspection machine for fasteners, including: an inspection station; a main dial rotatable through the inspection station and carrying thereon a plurality of fasteners; a reflective surface surrounding each of the plurality of fasteners to permit inspection light to reflect from the reflective surface and permit viewing of an entire outer circumference of a head of each of the plurality of fasteners to detect head cracks and bursts; and a lower surface of each of the plurality of fasteners being raised above the reflective surface. A method of optically inspecting fasteners is also provided.

14 Claims, 8 Drawing Sheets

OPTICAL INSPECTION SYSTEM AND METHOD OF USE

BACKGROUND OF THE INVENTION

1. Field of the Invention

The present invention relates to optical inspection systems generally and, more particularly, but not by way of limitation, to a novel optical inspection system that permits bright 360 degree inspection of the perimeter of the head of a fastener being inspected and a method of use thereof.

2. Background Art

A problem with conventional optical inspection machines is that, although the main dial and the in-line guide are constructed of a reflective material such as delrin plastic, the inspection light is not reflected well. Furthermore, there is a black band that tends to interfere with complete inspection of the head of the fastener.

Accordingly, it is a principal object of the present invention to provide an optical inspection system and method of use that affords a bright 360 degree view of the perimeter of the head of a fastener being inspected.

It is a further object of the present invention to provide such a system and method that is easily and economically implemented.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, an optical inspection machine for fasteners, comprising: an inspection station; a main dial rotatable through said inspection station and carrying thereon a plurality of fasteners; a reflective surface surrounding each of said plurality of fasteners to permit inspection light to reflect from said reflective surface and permit viewing of an entire outer circumference of a head of said each of said plurality of fasteners to detect head cracks and bursts; and a lower surface of said each of said plurality of fasteners being raised above said reflective surface. A method of optically inspecting fasteners is also provided.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which.

DETAILED DESCRIPTION OF THE PREFERRED EMBODIMENTS

Figure 1:
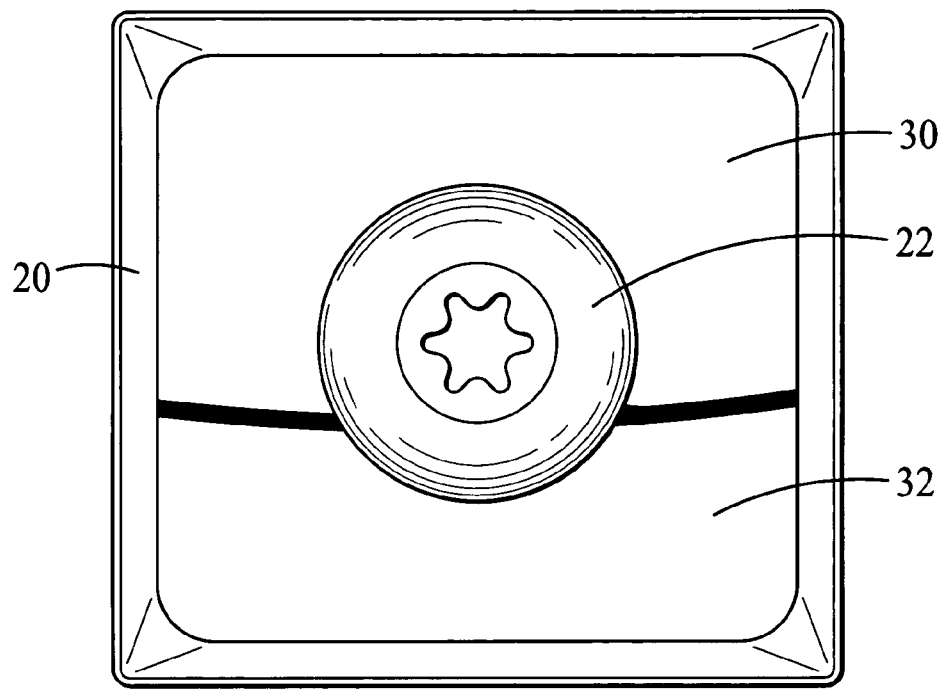
FIG. 1 is a top plan view of a fastener as seen on the monitor screen of a conventional optical inspection machine.

While the present invention is described with reference to a fastener with a round head, the present invention is applicable as well to fasteners having any configuration of head, hexagonal, square, etc., with appropriate changes being made to the construction of the optical inspection machine.

Reference should now be made to the drawing figures on which similar or identical elements are given consistent identifying numerals throughout the various figures thereof, and on which parenthetical references to figure numbers, when used, direct the reader to the view(s) on which the element(s) being described is (are) best seen, although the element(s) may be seen on other figures also.

FIG. 1 illustrates a monitor screen 20 on which is shown in top plan view the head of a fastener 22, the perimeter of the head of the fastener being inspected for head cracks and bursts. Fastener 22 is suspended from an opening defined in a circular rotating main dial 30, with the underside surface of the head resting against the surface of the main dial, and as the fastener passes through the inspection station, it passes a stationary in-line guide 32 that is disposed close to the main dial 30.

It will be understood that a number of fasteners are so disposed in main dial 30 having been fed thereon by a conventional feeder. If a burst or crack is detected in the head of fastener 22, the fastener is sent to a reject bin; otherwise, it is considered to be "good" and is sent to another bin.

A problem with conventional optical inspection machines noted above is that, although main dial 30 and in-line guide 32 are constructed of a reflective material such as delrin plastic, the inspection light is not reflected well. Furthermore, there is a black band between main dial 30 and in-line guide 32 that tends to interfere with complete inspection of the head of fastener 22.

Figure 2:
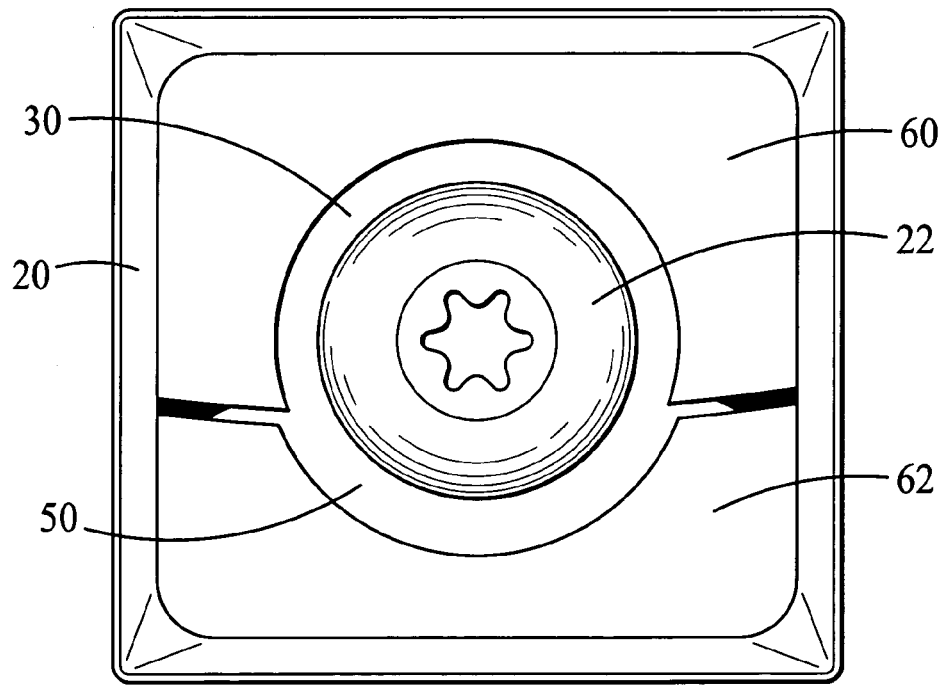
FIG. 2 is a top plan view of a fastener as seen on the monitor screen of an optical inspection machine constructed according to the present invention.

FIG. 2 is the same view as FIG. 1, but of a machine constructed according to the present invention. Here, the perimeter of the circumference of the head of fastener 22 appears to be seamlessly illuminated through 360 degrees. This is accomplished as shown on some of the drawing figures described below by raising the head of fastener 22 above main dial 30 and by adding a reflective guide plate 50, preferably of the same material as the main dial (neither the raising of the head or the reflective guide plate shown or clearly shown on FIG. 2). Black delrin plastic masks 60 and 62 are screwed, respectively, to main dial 30 and in-line guide 32 (FIG. 1) to limit the amount of reflected light in the inspection area surrounding the head to increase image contrast and to create a "back light" appearance of the image.

Figure 3:
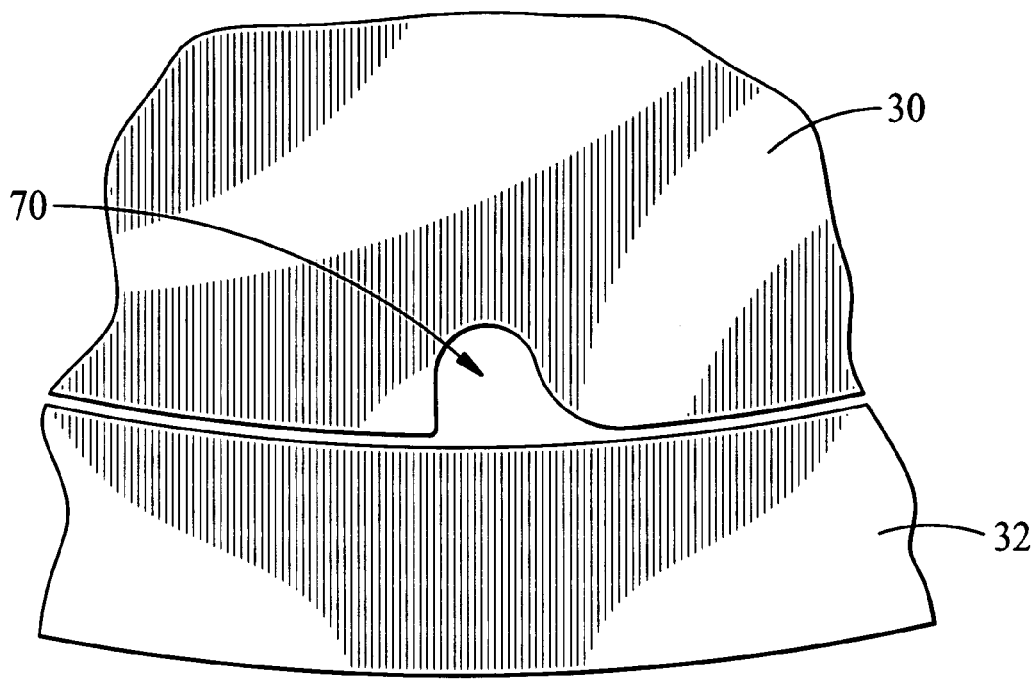
FIG. 3 is a top plan view of a portion of a conventional optical inspection machine.

FIG. 3 is the same as FIG. 1, without fastener 22, and shows opening 70 defined through main dial 30. As seen on FIG. 3 and as seen on some other figures described below and showing a conventional optical inspection machine and an optical inspection machine constructed according to the present invention, the leading edge of opening 70 is rounded to permit fastener 22 (FIG. 1, not shown on FIG. 3) to more easily enter the opening.

Figure 4:
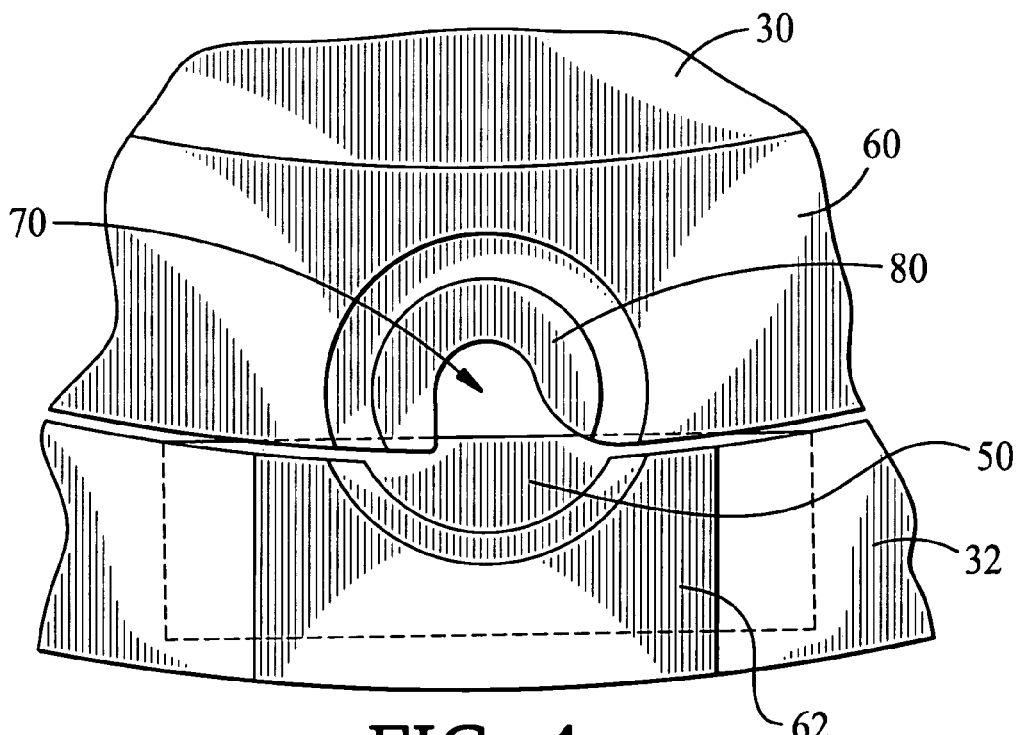
FIG. 4 is a top plan view of a portion of an optical inspection machine constructed according to the present invention.

FIG. 4 is the same as FIG. 2, without fastener 22, and shows opening 70 defined through main dial 30 and also shows more clearly reflective guide plate 50 screwed to the bottom of in-line guide plate 32. A raised arcuate land 80 is provided on which the head of fastener 22 (FIG. 2) rests. Land has a height above the upper surface of main dial 30 of approximately 0.090-inch and has a diameter about twenty percent or more less than the diameter of the head.

Figure 6:
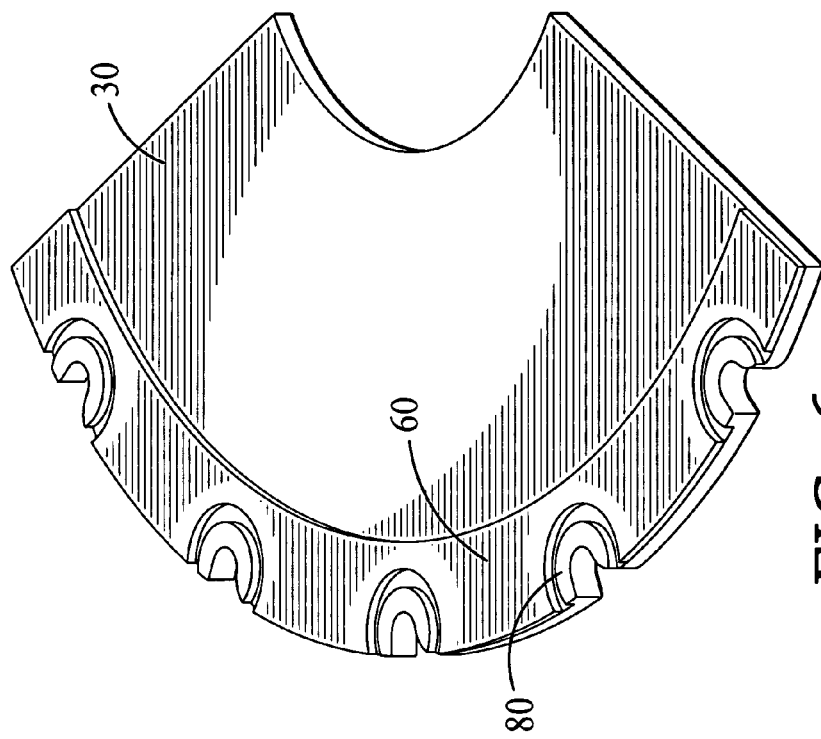
FIG. 6 is an isometric view of the construction of a portion of an optical inspection machine constructed according to the present invention.
Figure 5:
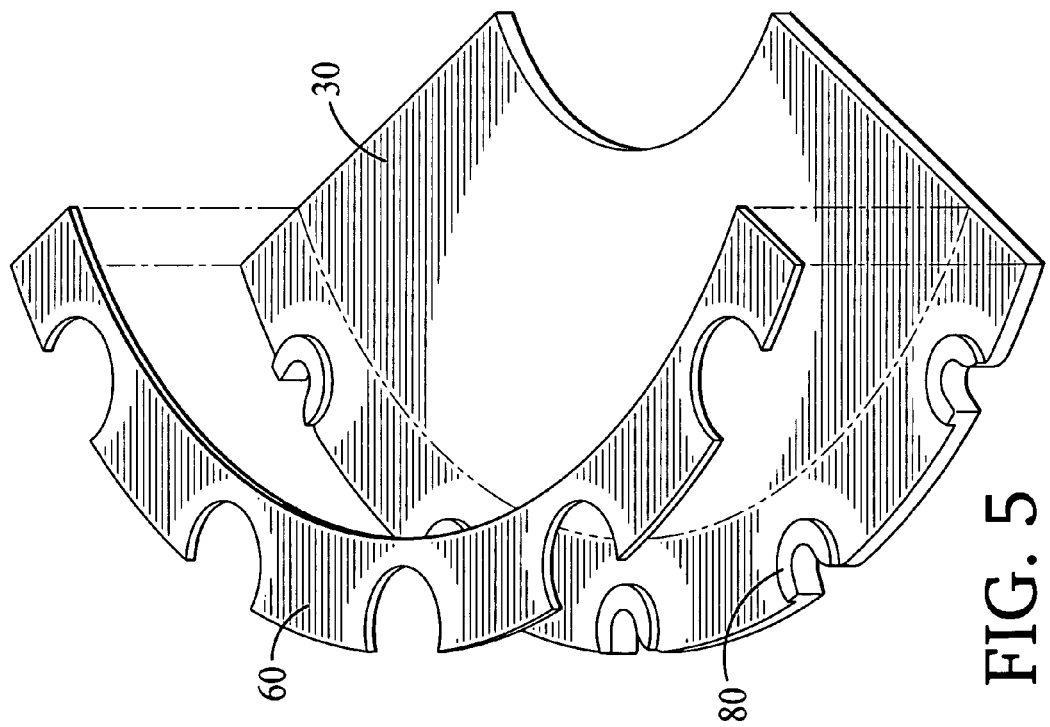
FIG. 5 is an exploded isometric view of the construction of a portion of an optical inspection machine constructed according to the present invention.

FIGS. 5 and 6 illustrate the construction of mask 60 and main dial 30. Main dial 30 may be conveniently manufactured in segments, as shown. It will be understood, however, that the segments of main dial 30 extend 360 degrees in a complete circle.

Figure 7:
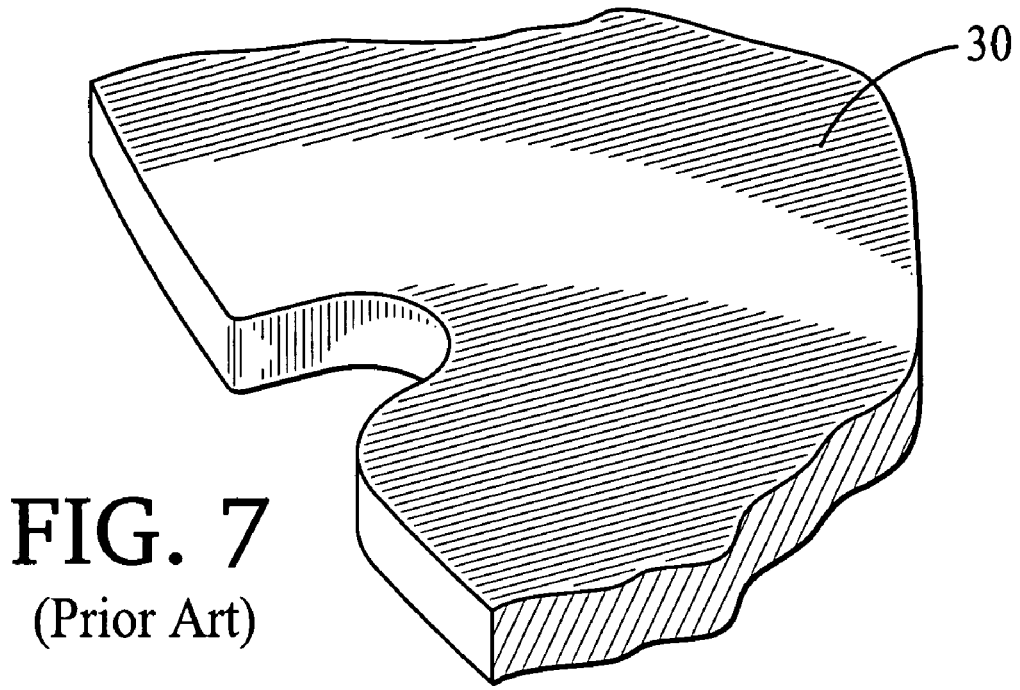
FIG. 7 is a fragmentary isometric view of part of the fastener holding portion of a conventional optical inspection machine.
Figure 8:
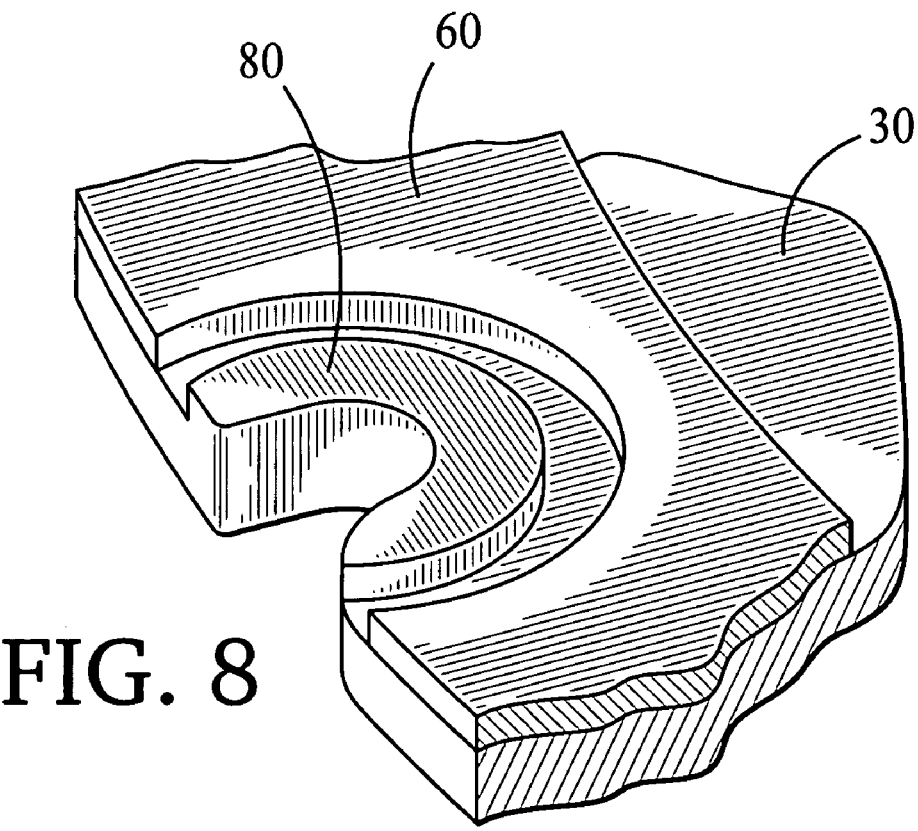
FIG. 8 is a fragmentary isometric view of part of the fastener holding portion of an optical inspection machine constructed according to the present invention.

FIGS. 7 and 8 illustrate in more detail some of the elements shown on FIGS. 3 and 4, respectively.

Figure 9:
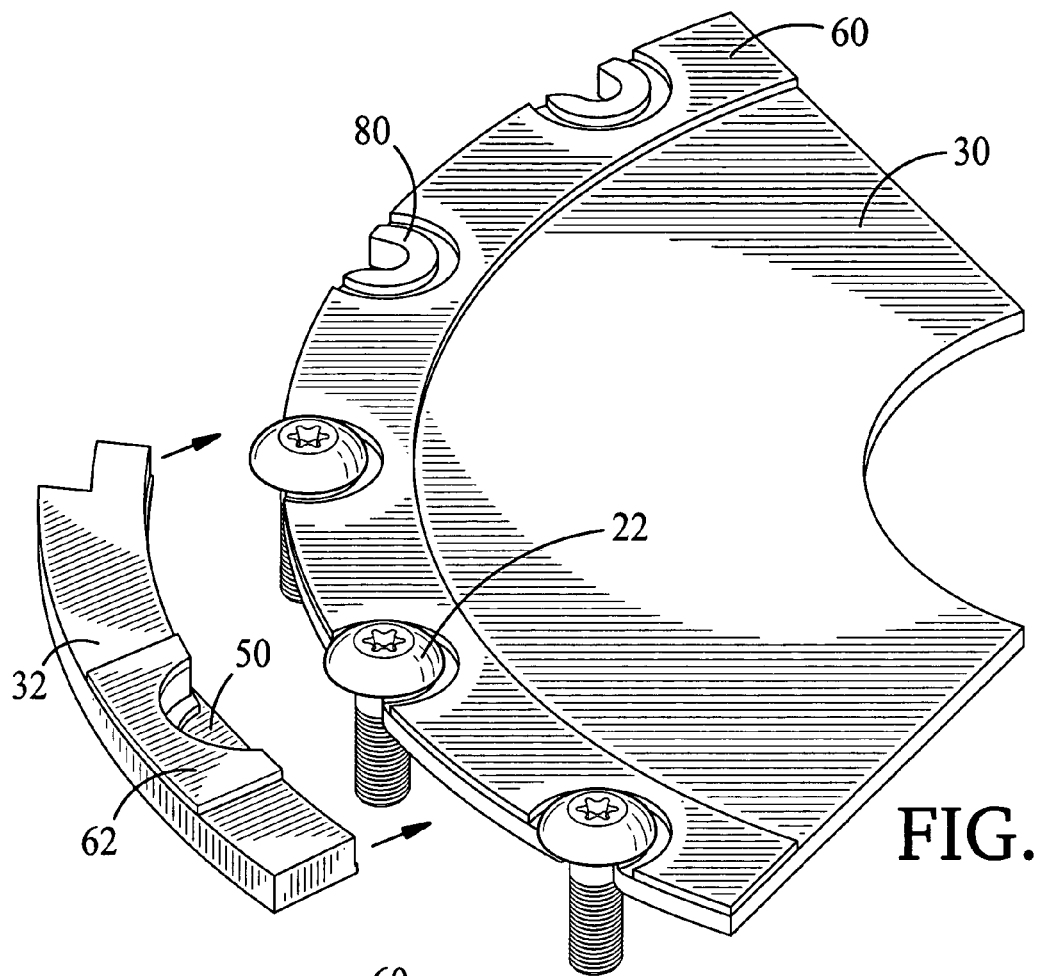
FIG. 9 is an exploded isometric view showing the construction of the fastener holding portion of an optical inspection machine constructed according to the present invention and showing how a stationary in-line guide fits adjacent the main dial.
Figure 10:
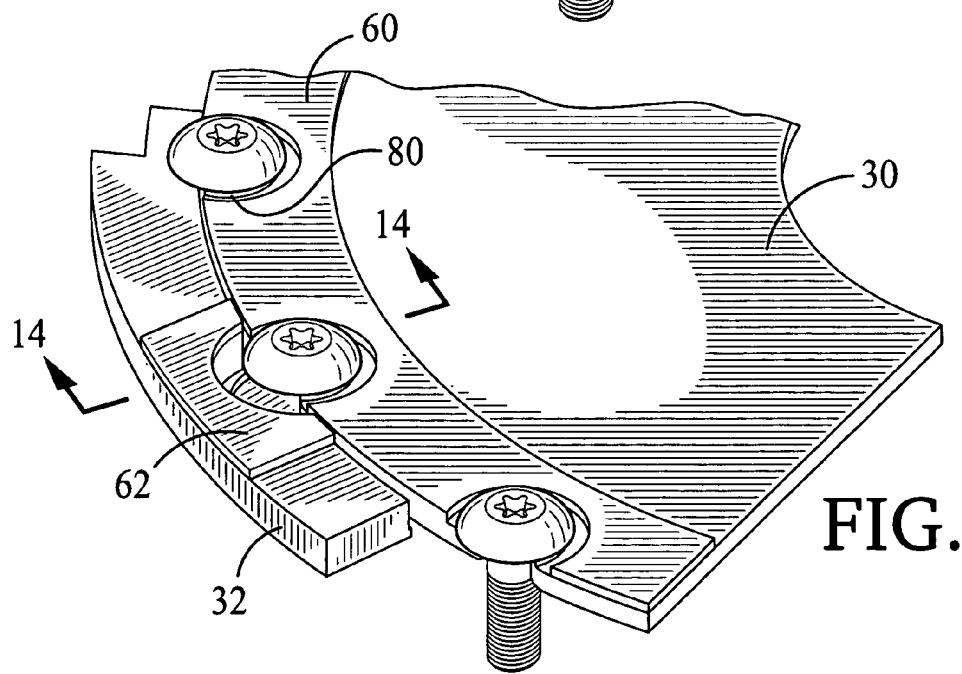
FIG. 10 is an isometric view shown the construction of the fastener holding portion of an optical inspection machine constructed according to the present invention and showing how an in-line guide fits adjacent the main dial.

FIGS. 9 and 10 illustrate in more detail how stationary in-line guide 32, with reflective guide plate 50 disposed underneath the in-line guide, fits adjacent main dial 30.

Figure 11:
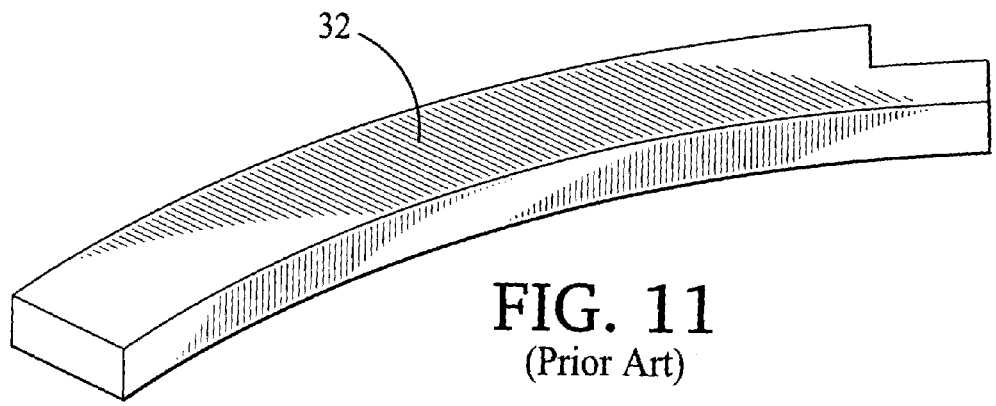
FIG. 11 is an isometric view of the in-line guide of a conventional optical inspection machine.

FIG. 11 illustrates in-line guide 32 of a conventional optical inspection machine and shows that the in-line guide is of solid one-piece construction.

Figure 12:
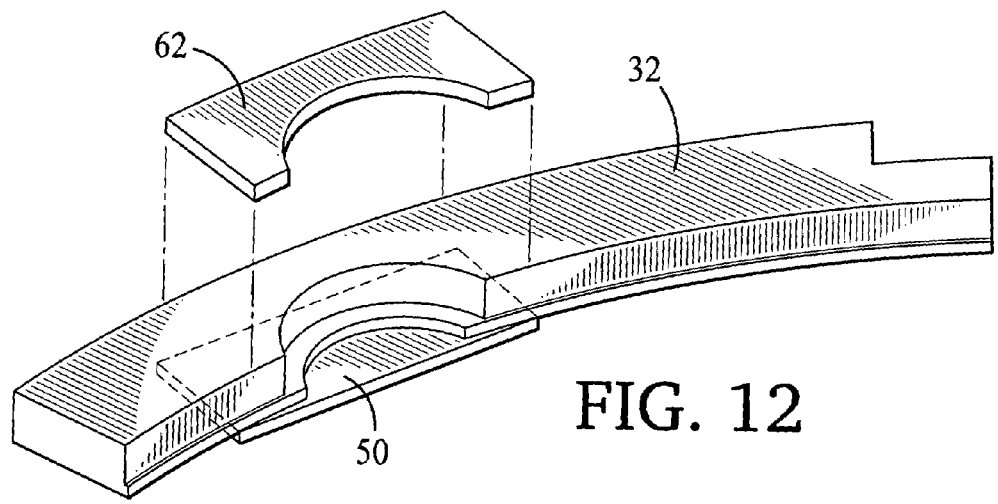
FIG. 12 is an exploded isometric view of the in-line guide of an optical inspection machine constructed according to the present invention.

FIG. 12 illustrates in-line 32 of the present invention and shows how mask 62 and reflective guide plate 50 are screwed to the in-line guide.

Figure 13:
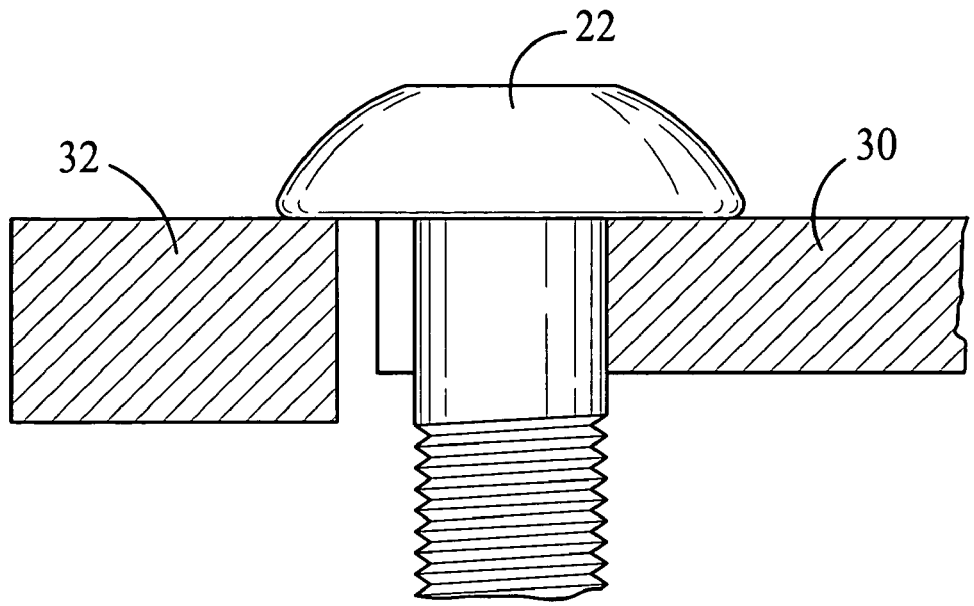
FIG. 13 is a side elevational view, partially in cross-section, of a fastener in a conventional optical inspection machine.

FIG. 13 illustrates a portion of a conventional optical inspection machine and shows fastener 22 with the underside of its head resting on main dial 30 and stationary in-line guide 32.

Figure 14:
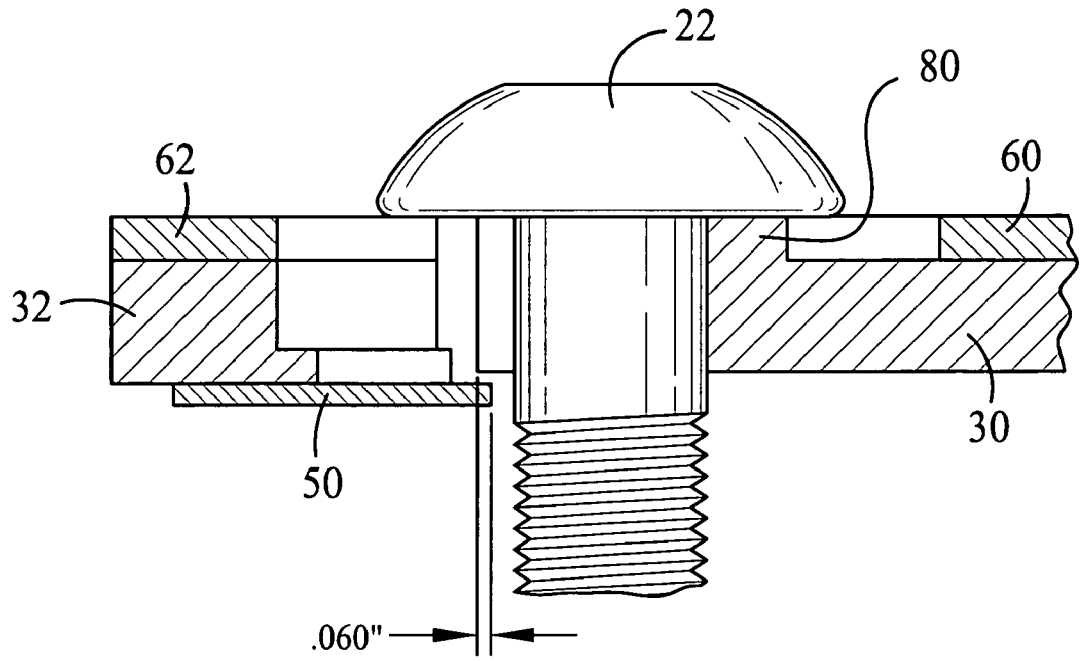
FIG. 14 is a side elevational view, partially in cross-section, of a fastener in an optical inspection machine constructed according to the present invention, the view being taken along line "14—14" of FIG. 10.

FIG. 14 illustrates a portion of an optical inspection machine constructed according to the present invention and shows the inside portion of the underside of fastener 22 resting on land 80 and elevated above the upper surface of main dial 30. It will be seen from FIG. 14 that the outside portion of the underside of the fastener does not rest on anything. Reflective guide plate 50 underlies main dial 30 by about 0.060-inch minimum as shown.

Figure 15:
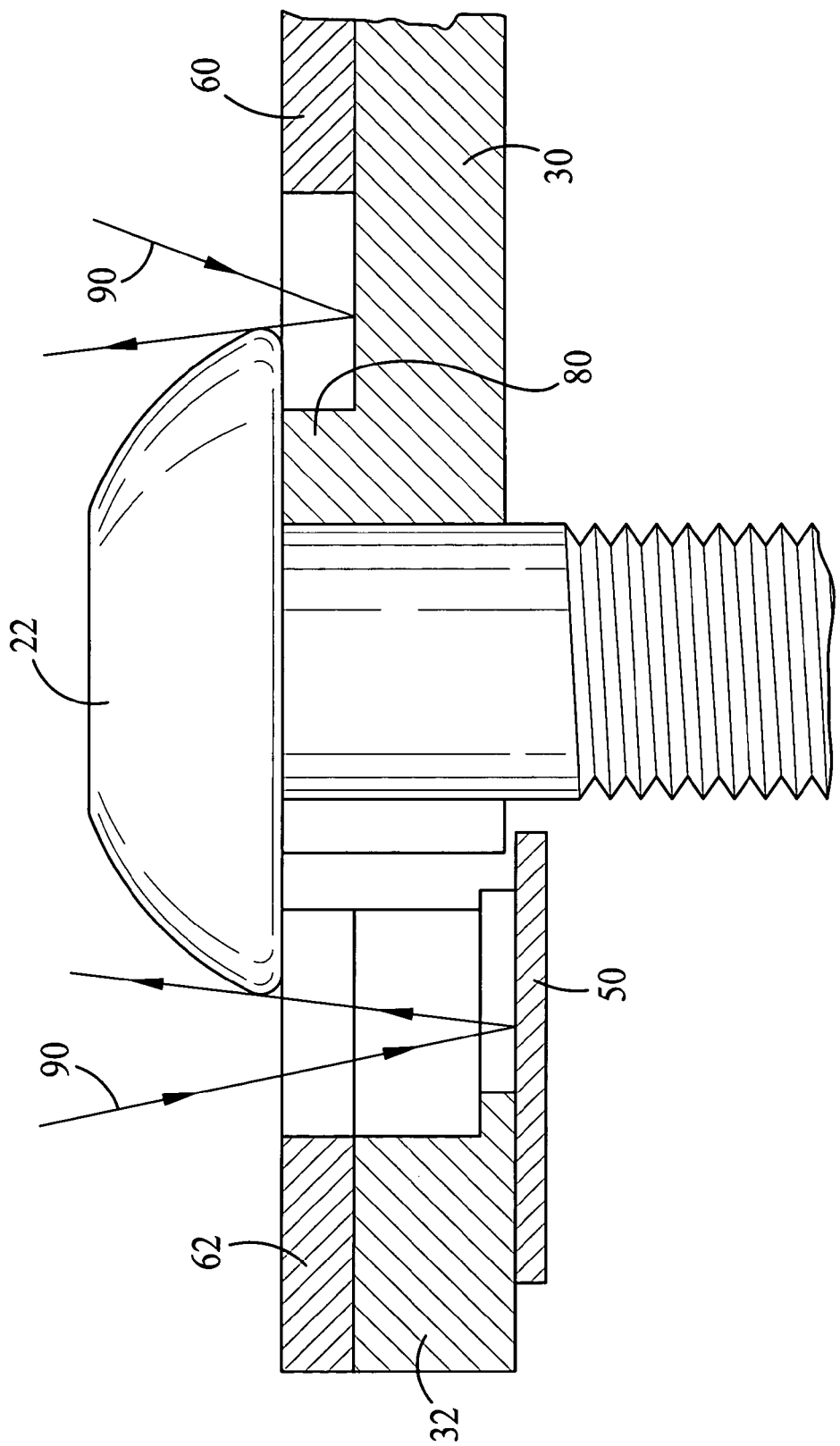
FIG. 15 is a side elevational view, partially in cross-section, of a fastener disposed in an optical inspection machine constructed according to the present invention and showing the paths of inspection light.

FIG. 15 is identical to FIG. 14, except that FIG. 15 indicates some of the paths of inspection light and how it is reflected, thus affording a 360 degree bright view of the perimeter of the head of fastener 22. Rays 90 indicate the paths of light that illuminate the perimeter of the head of fastener 22 to highlight cracks or bursts therein. Of course, rays 90 combine with similar rays (not shown on FIG. 15) to illuminate the entire 360-degree perimeter of the head of fastener 22.

Main dial 30 and in-line guide 32 (FIG. 1) are constructed of steel for machinability, but light up the same as aluminum when illuminated with the inspection light.

Masks 60 and 62 (FIG. 2) are constructed of black delrin plastic for white balance within the monitoring camera. The back of the delrin actually shows up somewhat darker that the delrin used on a conventional optical inspection machine. Main dial 30 (FIG. 2) is preferably constructed of Armoloy plated steel, a chromium plating, but can as well be constructed of white delrin plastic, or various steel and stainless steel materials. Whatever the material of construction, the surface should be smooth and shiny to reflect inspection light and preferable has a surface of RMS 15 or greater.

In the embodiments of the present invention described above, it will be recognized that individual elements and/or features thereof are not necessarily limited to a particular embodiment but, where applicable, are interchangeable and can be used in any selected embodiment even though such may not be specifically shown.

Spatially orienting terms such as "above", "below", "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. An optical inspection machine for fasteners, comprising:
    (a) an inspection station;
    (b) a main dial rotatable through said inspection station and carrying thereon a plurality of fasteners;
    (c) a reflective surface surrounding each of said plurality of fasteners to permit inspection light to reflect from said reflective surface and permit viewing of an entire outer circumference of a head of said each of said plurality of fasteners to detect head cracks and bursts; and
    (d) a lower surface of said each of said plurality of fasteners being raised above said reflective surface.

2. An optical inspection machine for fasteners, as defined in claim 1, further comprising: masks affixed to upper surfaces of said main dial and to a stationary in-line guide at said inspection station and surrounding said reflective surface.

3. An optical inspection machine for fasteners, as defined in claim 2, wherein: said masks are spaced apart from said outer circumference by a minimum of about 0.100-inch.

4. An optical inspection machine for fasteners, as defined in claim 1, wherein: each of said plurality of fasteners is raised above said reflective surface by about 0.090-inch.

5. An optical inspection machine for fasteners, as defined in claim 1, wherein each of said plurality of fasteners is raised above said reflective surface by a land having a width dimension at least about 20 percent less than a corresponding width dimension of a head of said fastener.

6. An optical inspection machine for fasteners, as defined in claim 2, further comprising: a reflective guide plate affixed to an undersurface of said in-line guide to reflect inspection light past a portion of a head of each of said plurality of fasteners.

7. An optical inspection machine for fasteners, as defined in claim 6, wherein: said reflective guide plate underlies said main dial by a minimum of about 0.060-inch.

8. A method of optically inspecting fasteners, comprising:
   (a) providing an inspection station;
   (b) providing a main dial rotatable through said inspection station and carrying thereon a plurality of fasteners;
   (c) providing a reflective surface surrounding each of said plurality of fasteners to permit inspection light to reflect from said reflective surface and permit viewing of an entire outer circumference of a head of each of said plurality of fasteners to detect head cracks and bursts; and
   (d) raising a lower surface of said each of said plurality of fasteners above said reflective surface.

9. A method of optically inspecting fasteners, as defined in claim 8, further comprising: affixing masks to upper surfaces of said main dial and to a stationary in-line guide at said inspection station and surrounding said reflective surface.

10. A method of optically inspecting fasteners, as defined in claim 9, further comprising: spacing said masks apart from said outer circumference by a minimum of about 0.100-inch.

11. A method of optically inspecting fasteners, as defined in claim 8, further comprising: raising each of said plurality of fasteners above said reflective surface by about 0.090-inch.

12. A method of optically inspecting fasteners, as defined in claim 8, further comprising: raising each said plurality of fasteners above said reflective surface with a land having a width dimension at least about 20 percent less than a corresponding width dimension of a head of said fastener.

13. A method of optically inspecting fasteners, as defined in claim 9, further comprising: affixing a reflective guide plate to an undersurface of said in-line guide to reflect inspection light past a portion of a head of each of said plurality of fasteners.

14. A method of optically inspecting fasteners, as defined in claim 13, further comprising: placing said reflective guide plate under said main dial by a minimum of about 0.060-inch.

* * * * *